United States Patent
Fischell et al.

(10) Patent No.: US 8,747,428 B2
(45) Date of Patent: Jun. 10, 2014

(54) CAROTID SHEATH WITH ENTRY AND TRACKING RAPID EXCHANGE DILATORS AND METHOD OF USE

(75) Inventors: Robert E. Fischell, Dayton, MD (US); Tim E. Fischell, Kalamazoo, MI (US)

(73) Assignee: Fischell Innovations, LLC, Dayton, MD (US)

( * ) Notice: Subject to any disclaimer, the term of this patent is extended or adjusted under 35 U.S.C. 154(b) by 0 days.

(21) Appl. No.: 13/349,060

(22) Filed: Jan. 12, 2012

(65) Prior Publication Data

US 2013/0184735 A1    Jul. 18, 2013

(51) Int. Cl.
*A61M 29/00* (2006.01)

(52) U.S. Cl.
USPC ............... 606/191; 606/194; 606/108

(58) Field of Classification Search
USPC ............. 606/108, 191–200; 604/103.04, 158, 604/160–161, 164.01, 164.1, 164.11, 604/170.01, 170.02, 264, 510; 600/184, 600/585
See application file for complete search history.

(56) References Cited

U.S. PATENT DOCUMENTS

| | | | |
|---|---|---|---|
| 4,195,624 A | * | 4/1980 | Douglas ............... 600/114 |
| 4,224,937 A | | 9/1980 | Gordon |
| 4,362,156 A | | 12/1982 | Feller, Jr. et al. |
| RE31,855 E | * | 3/1985 | Osborne ............... 604/161 |
| 4,705,511 A | | 11/1987 | Kocak |
| 4,862,891 A | * | 9/1989 | Smith ............... 606/191 |
| 4,976,689 A | | 12/1990 | Buchbinder et al. |
| 4,976,720 A | * | 12/1990 | Machold et al. ............... 606/194 |
| 4,997,421 A | | 3/1991 | Palsrok et al. |
| 5,069,674 A | | 12/1991 | Fearnot et al. |
| 5,158,543 A | * | 10/1992 | Lazarus ............... 604/164.1 |
| 5,180,376 A | | 1/1993 | Fischell |
| 5,324,262 A | | 6/1994 | Fischell et al. |
| 5,360,416 A | * | 11/1994 | Ausherman et al. ......... 604/272 |
| 5,360,432 A | | 11/1994 | Shtruman |
| 5,372,601 A | * | 12/1994 | Lary ............... 606/159 |
| 5,413,562 A | | 5/1995 | Swauger |
| 5,423,774 A | | 6/1995 | Fischell et al. |
| 5,454,795 A | | 10/1995 | Samson |
| 5,484,425 A | | 1/1996 | Fischell et al. |
| 5,496,344 A | | 3/1996 | Kanesaka et al. |
| 5,514,236 A | | 5/1996 | Avellanet et al. |
| 5,531,721 A | | 7/1996 | Pepin et al. |
| 5,630,802 A | * | 5/1997 | Moellmann et al. ..... 604/164.01 |
| 5,630,806 A | | 5/1997 | Inagaki et al. |
| 5,690,642 A | * | 11/1997 | Osborne et al. ............... 623/1.11 |
| 5,700,253 A | | 12/1997 | Parker |

(Continued)

FOREIGN PATENT DOCUMENTS

WO    WO2009045276    4/2009

OTHER PUBLICATIONS http://www.thefreedictionary.com/slot, definition of the term slot retrieved on May 23, 2013.*
Office Action dated Feb. 21, 2013 for U.S. Appl. No. 13/150,308.

(Continued)

*Primary Examiner* — David Eastwood
(74) *Attorney, Agent, or Firm* — Stoel Rives LLP

(57) ABSTRACT

Dilators and sheaths for use in minimally invasive vascular therapy are disclosed. In some embodiments, the dilators include a slot that accesses a guidewire lumen within the dilator. These slots facilitate rapid exchange of one dilator for another. In another embodiment, a dilator is sufficiently stiff to facilitate entry, but also designed to facilitate placement of the dilator along a tortuous path.

25 Claims, 3 Drawing Sheets

(56) References Cited

U.S. PATENT DOCUMENTS

| | | | |
|---|---|---|---|
| 5,702,373 A * | 12/1997 | Samson | 604/527 |
| 5,704,926 A | 1/1998 | Sutton | |
| 5,796,044 A | 8/1998 | Cobian et al. | |
| 5,797,948 A * | 8/1998 | Dunham | 606/194 |
| 5,827,230 A | 10/1998 | Bierman | |
| 5,827,239 A | 10/1998 | Dillon et al. | |
| 5,863,366 A | 1/1999 | Snow | |
| 5,879,499 A | 3/1999 | Corvi | |
| 5,895,402 A * | 4/1999 | Hundertmark et al. | 606/171 |
| 5,927,345 A | 7/1999 | Samson | |
| 5,944,697 A | 8/1999 | Biche | |
| 5,976,120 A | 11/1999 | Chow et al. | |
| 6,007,522 A * | 12/1999 | Agro et al. | 604/264 |
| 6,152,912 A | 11/2000 | Jansen et al. | |
| 6,165,163 A | 12/2000 | Chien et al. | |
| 6,338,725 B1 | 1/2002 | Hermann et al. | |
| 6,488,662 B2 * | 12/2002 | Sirimanne | 604/164.01 |
| 6,514,217 B1 * | 2/2003 | Selmon et al. | 600/585 |
| 6,533,770 B1 | 3/2003 | Lepulu et al. | |
| 6,863,674 B2 | 3/2005 | Kasahara et al. | |
| 6,939,337 B2 | 9/2005 | Parker et al. | |
| 7,083,588 B1 | 8/2006 | Schmulewitz et al. | |
| 7,320,697 B2 | 1/2008 | Demond et al. | |
| 7,331,966 B2 * | 2/2008 | Soma et al. | 606/108 |
| 7,438,712 B2 | 10/2008 | Chouinard | |
| 7,549,975 B2 * | 6/2009 | Lee et al. | 604/96.01 |
| 7,618,430 B2 | 11/2009 | Scheib | |
| 7,655,021 B2 | 2/2010 | Brasington et al. | |
| 7,708,744 B2 * | 5/2010 | Soma et al. | 606/108 |
| 7,815,762 B2 | 10/2010 | Lentz et al. | |
| 7,905,877 B1 | 3/2011 | Jimenez et al. | |
| 8,034,045 B1 | 10/2011 | Lyons | |
| 8,262,625 B1 | 9/2012 | Fischell et al. | |
| 2001/0001811 A1 * | 5/2001 | Burney et al. | 604/93.01 |
| 2001/0010247 A1 | 8/2001 | Snow | |
| 2001/0018576 A1 * | 8/2001 | Quinn | 604/264 |
| 2001/0044633 A1 | 11/2001 | Klint | |
| 2001/0047187 A1 * | 11/2001 | Milo et al. | 606/213 |
| 2002/0072732 A1 * | 6/2002 | Jung et al. | 604/535 |
| 2002/0077600 A1 * | 6/2002 | Sirimanne | 604/164.1 |
| 2002/0169377 A1 * | 11/2002 | Khairkhahan et al. | 600/433 |
| 2003/0083691 A1 * | 5/2003 | Wantink | 606/194 |
| 2003/0093060 A1 | 5/2003 | Kempf | |
| 2003/0120213 A1 * | 6/2003 | Nash et al. | 604/160 |
| 2003/0199826 A1 * | 10/2003 | Windheuser et al. | 604/161 |
| 2003/0225365 A1 * | 12/2003 | Greff et al. | 604/43 |
| 2003/0229313 A1 | 12/2003 | Bierman | |
| 2004/0010243 A1 | 1/2004 | Klint | |
| 2004/0116960 A1 | 6/2004 | Demond et al. | |
| 2004/0133225 A1 * | 7/2004 | Makower | 606/167 |
| 2004/0153049 A1 | 8/2004 | Hewitt et al. | |
| 2004/0236346 A1 | 11/2004 | Parker | |
| 2004/0267196 A1 * | 12/2004 | Miki et al. | 604/103.04 |
| 2005/0021022 A1 | 1/2005 | Sturm et al. | |
| 2005/0049696 A1 * | 3/2005 | Siess et al. | 623/2.11 |
| 2005/0060017 A1 | 3/2005 | Fischell et al. | |
| 2005/0149060 A1 | 7/2005 | Thorstenson et al. | |
| 2005/0209533 A1 * | 9/2005 | Lorenz | 600/585 |
| 2005/0228479 A1 * | 10/2005 | Pavcnik et al. | 623/1.11 |
| 2006/0064054 A1 | 3/2006 | Sakakine et al. | |
| 2006/0089618 A1 | 4/2006 | McFerran et al. | |
| 2006/0095050 A1 | 5/2006 | Hartley et al. | |
| 2006/0155302 A1 | 7/2006 | Sisken et al. | |
| 2007/0066958 A1 | 3/2007 | Wright | |
| 2007/0118207 A1 | 5/2007 | Amplatz et al. | |
| 2007/0185416 A1 * | 8/2007 | Melsheimer | 600/585 |
| 2007/0185521 A1 * | 8/2007 | Bui et al. | 606/191 |
| 2007/0219500 A1 | 9/2007 | Wright et al. | |
| 2008/0051758 A1 * | 2/2008 | Rioux et al. | 604/509 |
| 2008/0097516 A1 | 4/2008 | Chang et al. | |
| 2008/0114374 A1 * | 5/2008 | Soma et al. | 606/108 |
| 2009/0018525 A1 * | 1/2009 | Waite et al. | 604/508 |
| 2009/0030400 A1 * | 1/2009 | Bose et al. | 604/510 |
| 2009/0054845 A1 | 2/2009 | Puhasmagi et al. | |
| 2009/0088790 A1 * | 4/2009 | Parodi et al. | 606/200 |
| 2009/0157162 A1 * | 6/2009 | Chow et al. | 623/1.11 |
| 2009/0234295 A1 | 9/2009 | Lampropoulos et al. | |
| 2009/0240202 A1 | 9/2009 | Drasler et al. | |
| 2009/0240213 A1 * | 9/2009 | Miyagawa et al. | 604/264 |
| 2009/0287182 A1 | 11/2009 | Bishop et al. | |
| 2009/0306591 A1 | 12/2009 | Amisar et al. | |
| 2009/0306603 A1 | 12/2009 | Bierman et al. | |
| 2010/0016837 A1 | 1/2010 | Howat | |
| 2010/0049168 A1 | 2/2010 | Parker et al. | |
| 2010/0114147 A1 * | 5/2010 | Biyani | 606/191 |
| 2011/0087234 A1 * | 4/2011 | Ayala et al. | 606/108 |
| 2011/0160702 A1 | 6/2011 | Jimenez et al. | |
| 2011/0245775 A1 | 10/2011 | Tekulve | |
| 2012/0215174 A1 | 8/2012 | Fischell et al. | |
| 2012/0265282 A1 | 10/2012 | Fischell et al. | |

OTHER PUBLICATIONS

Office Action dated Sep. 21, 2012 for U.S. Appl. No. 13/150,308.
Restriction Requirement dated Nov. 18, 2011 for U.S. Appl. No. 13/032,876.
Office Action dated Dec. 8, 2011 for U.S. Appl. No. 13/032,876.
Office Action dated Mar. 1, 2012 for U.S. Appl. No. 13/032,876.
Office Action dated May 25, 2012 for U.S. Appl. No. 13/032,876.
International Search Report and Written Opinion dated Aug. 7, 2012 for PCT/US2012/035268.
Notice of Allowance dated Oct. 16, 2012 for U.S. Appl. No. 13/032,876.
International Search Report and Written Opinion dated Nov. 8, 2012 for PCT/US2012/40391.
International Search Report and Written Opinion dated Sep. 24, 2012 for PCT/US2012/043243.
Notice of Allowance dated Jul. 9, 2013 for U.S. Appl. No. 13/150,308.
Notice of Allowance dated Jul. 26, 2013 for U.S. Appl. No. 13/431,526.
International Search Report and Written Opinion dated Jul. 18, 2013 for PCT/US2013/033840.
Office Action dated Mar. 6, 2013 for U.S. Appl. No. 13/431,526.
Office Action dated Mar. 19, 2013 for U.S. Appl. No. 13/085,951.
International Search Report and Written Opinion dated Apr. 25, 2013 for PCT/US2013/020941.

* cited by examiner

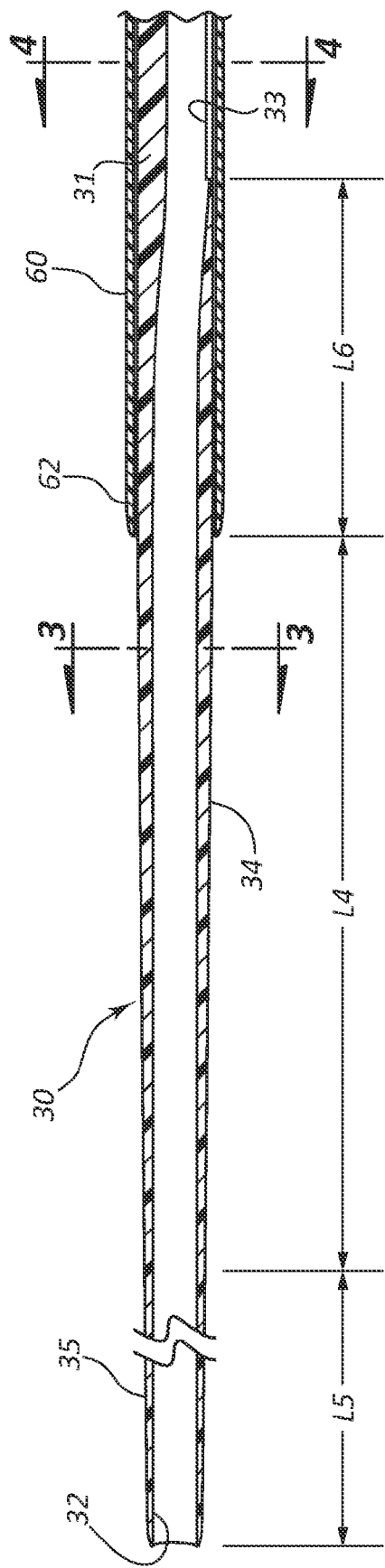
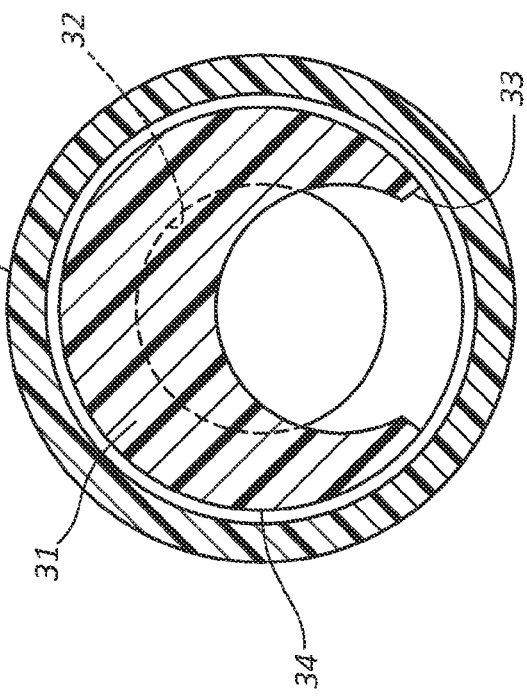
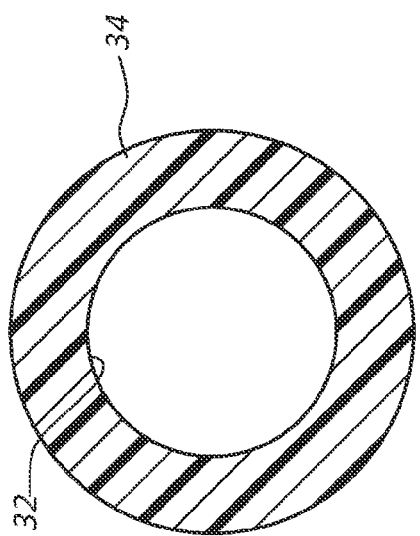
FIG. 2
FIG. 4
FIG. 3

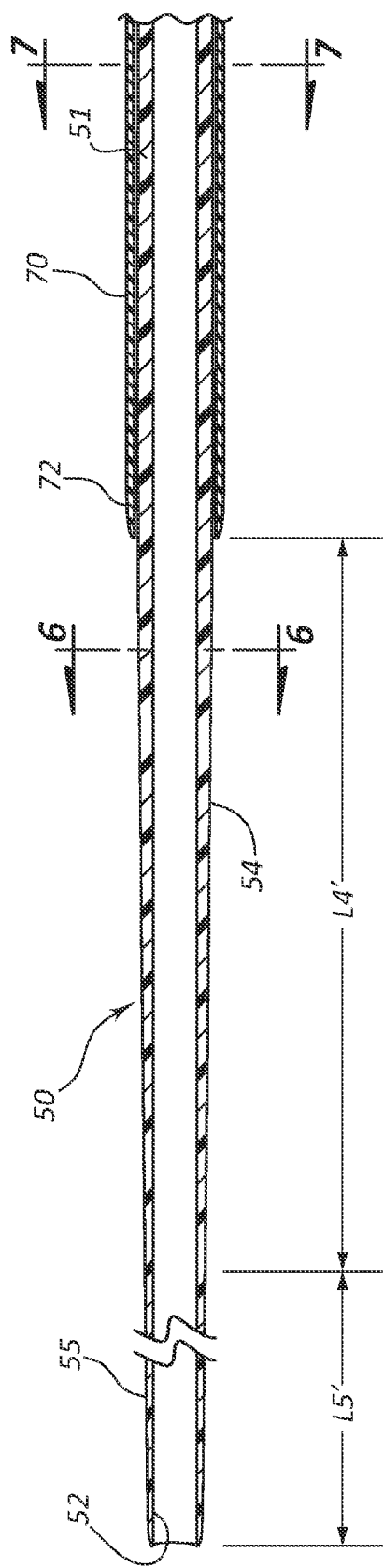
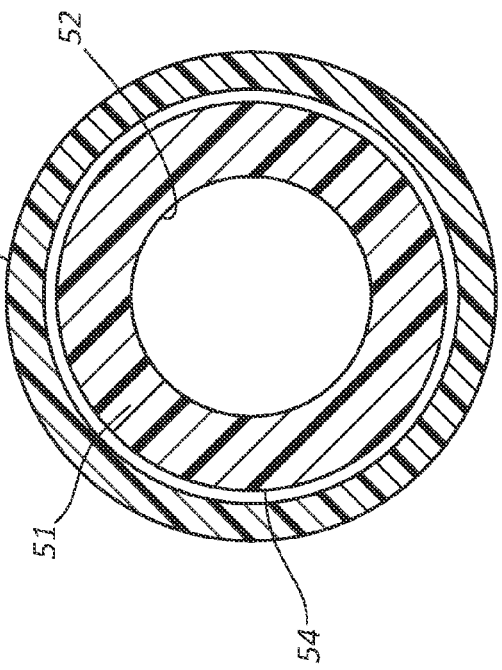
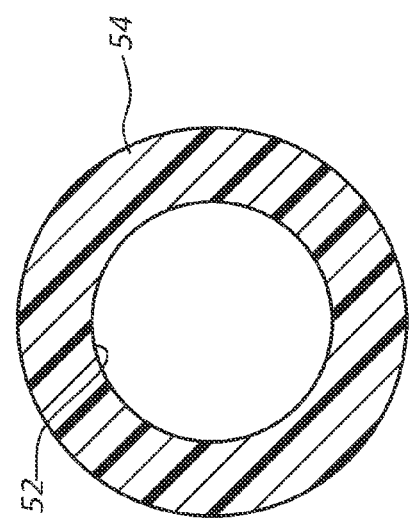
FIG. 5
FIG. 7
FIG. 6

CAROTID SHEATH WITH ENTRY AND TRACKING RAPID EXCHANGE DILATORS AND METHOD OF USE

TECHNICAL FIELD

The present disclosure relates generally to minimally invasive treatment devices such as sheaths, catheters, and dilators. More specifically, the present disclosure relates to sheaths, catheters, and dilators for use with treatments within the human vasculature, including the carotid artery.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 2 is a longitudinal cross section of one embodiment of a rapid exchange tracking dilator disposed within a carotid sheath.

FIG. 3 is a transverse cross sectional view of the tracking dilator of FIG. 2, taken through line 3-3.

FIG. 4 is a transverse cross sectional view of the tracking dilator of FIG. 2, taken through line 4-4.

FIG. 5 is a longitudinal cross section of a dilator disposed within a carotid sheath.

FIG. 6 is a transverse cross sectional view of a portion of the dilator of FIG. 5, taken through line 6-6.

FIG. 7 is a transverse cross sectional view of a portion of the dilator of FIG. 5, taken through line 7-7.

DETAILED DESCRIPTION

Figure 1:
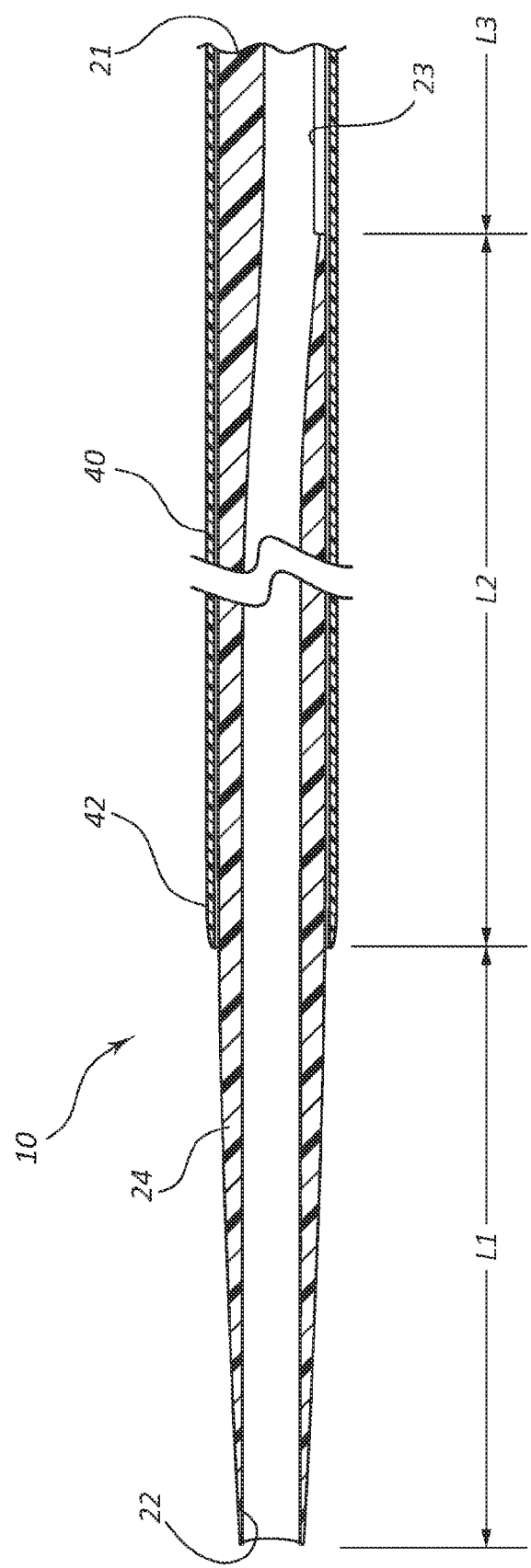
FIG. 1 is a longitudinal cross section of portions of one embodiment of a rapid exchange entry dilator and a carotid sheath.

Catheters, sheaths, dilators, guidewires, and other treatment devices are used in connection with minimally invasive treatments and therapies, such as minimally invasive therapies within the human vasculature. The disclosure below relates specifically to, among other things, the placement and use of such devices to access and treat stenosis or other obstructions within the carotid artery. Notwithstanding these specific examples and references, the current disclosure is applicable to any treatment involving disposition of elongate devices within body lumens.

In some procedures, stents, balloons, filters, or other treatment devices are advanced within the vasculature of a patient through use of elongate catheters or sheaths. Furthermore, such sheaths or catheters can be placed, advanced, retracted, or moved in connection with dilators and/or guidewires. Specifically, in some instances, an elongate sheath or guiding catheter is disposed within the vasculature such that its distal end accesses a portion of the carotid artery. Such a sheath or guiding catheter may be designed to provide therapy within the vasculature or may be used as a conduit to advance other instruments, for example a catheter containing a stent or other treatment device, to the treatment site. In some instances, the sheath or guiding catheter is placed and positioned through use of dilators and/or guidewires. As used herein, a "carotid sheath" refers to a sheath or catheter configured to provide access to the carotid artery.

It will be readily understood that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner while the practitioner is using or manipulating the device, while the distal end is the opposite end. For example, the proximal end of a catheter or sheath used in minimally invasive vascular treatment is the end accessible to a practitioner during use, while the distal end is disposed within a patient during use.

The "axial direction" of an elongate component refers to a direction along the center axis of the elongate component.

In some instances, a practitioner accesses the carotid artery by an entry point in the femoral artery. A relatively small catheter and/or guidewire can then be advanced from the femoral artery to the aortic arch, and from the aortic arch to either the right or left common carotid artery (in some instances via the innominate artery in the case of the right common carotid artery). Access to the internal or external carotid arteries is generally gained via either common carotid artery. The initial catheter and/or guidewire can then be used to help position subsequent stiffer catheters or guidewires.

An access path from the aortic arch to either common carotid artery, and any subsequent branch thereof, can be relatively tortuous. In some instances, carotid sheaths configured to act as conduits for stent delivery devices are relatively stiff and thus difficult to position within this tortuous path. Inability to properly place a carotid sheath can make minimally invasive stenting impossible, thus resulting in more invasive procedures such as surgical endarterectomy.

An exemplary procedure includes first gaining access to the vascular system through the femoral artery at the groin. In some instances, a needle and/or a guidewire is utilized at this step. A physician then advances a guidewire and/or a diagnostic catheter (e.g., a small catheter size 5 or 6 French) from the entry point to the aortic arch, then from the aortic arch to the common carotid artery. In some instances, the guidewire and/or diagnostic catheter is further advanced into the internal or external carotid arteries. The diagnostic catheter can then be utilized to advance a stiff guidewire to the treatment site. During the course of some procedures, the distal end of the stiff guidewire remains anchored in one of these distal positions during the treatment. In an exemplary procedure, a physician then uses an entry and/or a tracking dilator to introduce and advance a sheath into the entry point and to a position just proximal of the treatment location. Such positioning of the sheath allows a practitioner to utilize the sheath to advance treatment devices, such as balloons, stents, and so on, to the treatment site. In some instances, the sheath is very stiff. In such instances, use of a tracking dilator to advance the relatively stiff sheath can reduce the risk that the sheath will cause the distal end of the stiff guidewire to become displaced from its anchor location.

As further described below, in some embodiments, one or more dilators are utilized in connection with advancing a carotid sheath to a treatment location. As used herein, "dilator" refers to an elongate instrument that may be configured to be disposed within an elongate sheath, the dilator configured to guide the sheath as the sheath is advanced along a path. In some embodiments, the dilator is relatively stiff or resilient to aid in advancing the dilator and/or sheath beyond points of high resistance, such as through an arterial wall at the access point (for example, in instances where scar tissue or calcification make access particularly difficult). Some dilators include lumens configured to accommodate other instruments such as guidewires. Moreover, in certain of the embodiments described below, a dilator includes features configured to facilitate rapid exchange between dilators. For instance, as detailed below, some dilators within the scope of this disclosure include a slot to facilitate rapid exchange. Rapid exchange is utilized, for example, in instances where a first dilator is used primarily for entry (an "entry dilator"), while a second dilator is used to advance a sheath along a distal tortuous path, such as from the aortic arch to the carotid artery (a "tracking dilator").

FIG. 1 is a longitudinal cross section of portions of one embodiment of a rapid exchange entry dilator 10 and a carotid sheath 40. As illustrated, the distal end of each component is positioned to the left of the proximal end. In the illustrated embodiment, only a portion (adjacent the distal ends) of each component is shown, as indicated by the cut-away lines on the right side of the drawing.

The illustrated entry dilator 10 includes an elongate main body 21 configured to be disposed within the carotid sheath 40. The carotid sheath 40 is configured with a radiopaque marker band 42, which in some embodiments is positioned at or adjacent the distal end of the carotid sheath 40. The entry dilator 10 of FIG. 1 further includes a central lumen 22 configured to accommodate a guidewire (not shown). In some embodiments the central lumen 22 is sized to accommodate particular sizes of guidewires, such as guidewires from about 0.012 inches to about 0.038 inches, including guidewires from about 0.018 inches to about 0.032 inches and from about 0.022 inches to about 0.028 inches.

In some embodiments the entry dilator 10 and the carotid sheath 40 are displaceable with respect to each other in the axial direction of each component. During certain therapies, however, the two components are advanced or retracted within the vasculature together, meaning the two components are moved as a unit, without axial displacement with respect to each other. Additionally, some instances, the two components are advanced by a combination of moving the components together and displacing them with respect to each other.

In embodiments where the entry dilator 10 and the carotid sheath 40 are advanced together, distance L1 is the length of the portion of the entry dilator 10 that extends from the distal end of the carotid sheath 40. In some embodiments L1 is from about 2 cm to about 8 cm in length, including lengths from about 3 cm to about 7 cm and lengths from about 4 cm to about 6 cm. Because, in certain embodiments, the entry dilator 10 is displaceable with respect to the carotid sheath 40, distance L1 may not be a constant value, but rather represent a general parameter. In other embodiments, L1 represents the maximum distance the entry dilator 10 is configured to extend from the carotid sheath 40. In other words, in some examples, the entry dilator 10 is configured to be displaceable with respect to the carotid sheath 40, up to a certain point, but can further include a coupling mechanism (e.g., a luer fitting on the proximal end) configured to limit the maximum displacement of the distal end of the entry dilator 10 with respect to the carotid sheath 40.

In some embodiments, the entry dilator 10 includes an eccentrically located slot 23. (A transverse cross sectional view of an analogous slot in another embodiment of a dilator is also shown in FIG. 4.) As further outlined below, the slot 23 of FIG. 1 is configured to facilitate rapid exchange of the entry dilator 10 with another dilator. In the illustrated embodiment, the slot 23 is configured as an elongate opening in the sidewall of the entry dilator 10 that is in communication with the central lumen 22. The slot 23 extends to the proximal end of the entry dilator 10. Distance L2 shown in FIG. 1 represents the distance from the distal end of the carotid sheath 40 to the beginning of the slot 23. In other words, L2 is the length of the entry dilator 10 that is disposed within the carotid sheath 40 but does not include the slot 23. In some embodiments L2 is from about 5 cm to about 15 cm, including embodiments from about 7 cm to about 12 cm and from about 9 cm to about 11 cm.

The illustrated entry dilator 10 has a tapered portion 24 adjacent the distal end of the entry dilator 10. In some embodiments the tapered portion 24 is configured to extend completely from the carotid sheath 40; that is, in some embodiments the tapered portion 24 has a length of L1. In other embodiments the tapered portion 24 is longer or shorter than L1.

In the illustrated embodiment, distance L3 corresponds to the length of the entry dilator 10 and carotid sheath 40 from the distal end of the slot 23 to the proximal end (not shown) of the carotid sheath 40. In some embodiments the entry dilator 10 extends proximally from the proximal end of the carotid sheath 40, while in other embodiments it is flush with or shorter than the carotid sheath 40 at the proximal end. In some embodiments L3 is from about 60 to 100 cm, including embodiments from about 70 cm to 90 cm and embodiments from about 75 cm to about 85 cm. In certain embodiments, the carotid sheath 40 includes a luer fitting at the proximal end, including luers that are coupleable to a Touhy-Borst fitting.

In the illustrated embodiment, entry dilator 10 is configured to facilitate entry into the vasculature. For example, in some embodiments entry dilator 10 is relatively stiff (compared to, for example, the tracking dilator described below) in order to facilitate entry through calcified arteries, such as the femoral artery. In certain embodiments, the entry dilator 10 is thus composed of a relatively stiff material, for example, polypropylene or nylon. Moreover, in some embodiments the material used for the dilator has a durometer hardness equal to or greater than 50 on the Shore D scale, including materials having a hardness from about 50 to about 80 on the Shore D scale, or materials having a hardness from about 60 to about 70 on the Shore D scale.

FIG. 2 is a longitudinal cross section of a tracking dilator 30 disposed within a carotid sheath 60. While FIG. 1 illustrates the entry dilator 10 and FIG. 2 illustrates the tracking dilator 30, certain elements and subcomponents of each can, in certain respects, resemble elements and subcomponents of the other. It will be appreciated that all the illustrated embodiments may have analogous features. Accordingly, the relevant descriptions of such features apply equally to the features of the tracking dilator 30 and the related components of FIG. 2. Any suitable combination of the features, and variations of the same, described with respect to the components illustrated in FIG. 1 can be employed with the components of FIG. 2, and vice versa. Furthermore, analogous or substantially analogous features shown in one figure may or may not be designated by a reference numeral regardless of whether the analogous feature is so designated in the analogous figure. This pattern of disclosure applies equally to further embodiments and components described herein.

FIG. 2 shows the tracking dilator 30 disposed within a carotid sheath 60. As with the carotid sheath 40 of FIG. 1, the carotid sheath 60 of FIG. 2 includes a radiopaque marker band 62. In the illustrated embodiment, the tracking dilator 30 includes a main body 31 with a central lumen 32 disposed within the main body 31. In some embodiments, the central lumen 32 is configured to accommodate a guidewire, analogous to the central lumen 22 of FIG. 1. Furthermore, the tracking dilator 30 shown in FIG. 2 includes an eccentrically placed slot 33. In the illustrated embodiment, the slot 33 is located a distance, L6, from the distal end of the carotid sheath 60. In some embodiments L6 is from about 60 to 100 cm, including embodiments from about 70 cm to 90 cm and embodiments from about 75 cm to about 85 cm. Like the slot 23 of FIG. 1, the slot 33 of the tracking dilator 30 of FIG. 2 extends from the position shown to the proximal end (not shown) of the tracking dilator 30.

As further detailed below, in some embodiments, the tracking dilator 30 is configured to facilitate access to relatively tortuous portions of the vasculature. For example, in some procedures, a relatively small-diameter needle is inserted into the femoral artery at the access point and a thin guidewire is inserted through the needle. In the exemplary procedure, the needle is then removed and an entry dilator (such as 10 from FIG. 1) is advanced along the guidewire. As described above, the entry dilator 10 of FIG. 1 is relatively stiff, allowing it to be forced through the artery wall or through calcified tissue in the artery, thereby providing fuller access to the vasculature. In some instances the entry dilator 10 is then exchanged for the tracking dilator 30 in order to traverse tortuous paths within the vascular, for example, traversing from the aortic arch to the common carotid artery or beyond. In some procedures, the carotid sheath 40 is advanced with the tracking dilator 30.

In some embodiments, the slot 23, 33 of the dilator 10, 30 facilitates rapid exchange of one dilator 10, 30 for another. For example, in some procedures where a practitioner wishes to replace dilator "A" disposed within the body with dilator "B," slots on each dilator facilitate this exchange. In this example, a guidewire is disposed within dilator A. If dilator A were to be removed over the proximal end of the guidewire, the length of guidewire disposed outside the body would need to be longer than the total length of dilator A, in order to allow a practitioner to remove the dilator while still being able to directly grasp (or otherwise secure) the guidewire. A slot in the dilator, however, allows the practitioner to decouple the dilator from the guidewire via the slot, allowing the practitioner to maintain direct contact with the guidewire near the insertion point. Only the distal-most portion of dilator A (having no slot) would need to be fed over the proximal end of the guidewire. Similarly, when the practitioner replaces dilator A with dilator B, the distal end (having no slot) of dilator B can be slid over the proximal end of the guidewire while the rest of the dilator could be fed onto the guidewire via the slot. Thus, as long as the guidewire extends from the patient a distance greater than the length of the non-slotted portions of each dilator, a practitioner can quickly exchange dilators while maintaining secure contact with the guidewire near the insertion point.

The features of tracking dilator 30 of FIG. 2 are configured to facilitate advancement of the tracking dilator 30 along relatively tortuous paths. In some embodiments, the tracking dilator 30 includes a cylindrical portion 35 adjacent the distal end of the tracking dilator 30. The cylindrical portion 35 defines a constant outside diameter along its length, L5. L5 is from about 3 cm to about 15 cm in some embodiments, including embodiments from about 5 cm to about 12 cm and embodiments from about 7 cm to about 11 cm. Furthermore, in some embodiments, the cylindrical portion 35 is formed in a relatively thin walled design, the wall of the dilator being less than 0.025 inches in some instances, including wall thicknesses of less than 0.020 inches, less than 0.015 inches, and less than 0.010 inches. Moreover, the tracking dilator 30 of some embodiments is composed of a relatively soft material, for example an elastomer with a durometer hardness that is less than or equal to 45 on the Shore D scale. In some instances, the tracking dilator 30 is softer than, for example, an entry dilator, such as the entry dilator 10 of FIG. 1, or a carotid sheath, such as the carotid sheathes 40, 60 of FIGS. 1 and 2.

In certain procedures, the softness of the tracking dilator 30 and/or the thin walled design of the cylindrical portion 35 facilitates advancement of the tracking dilator along a tortuous path. Stiffer dilators, for example the entry dilator 10 of FIG. 1, may be more difficult to advance over relatively tortuous paths. Furthermore, the design of the tracking dilator 30 may lower the risk of displacing the distal end of a guidewire used to place the tracking dilator 30, as compared to stiffer dilators.

In some embodiments, the tracking dilator 30 includes a tapered portion 34 adjacent the cylindrical portion 35. In the illustrated embodiment, the tapered portion 34 is configured as a transition portion between the more pliable cylindrical portion 35 and the stiffer proximal portion of the tracking dilator 30. In the exemplary embodiment, the tracking dilator 30 thus has a pliable tip to facilitate advancement of the tracking dilator 30 along a difficult path while also having a stiffer portion along the length of the tracking dilator 30. This stiffer portion is configured to facilitate in advancing the relatively stiff carotid sheath 60 to the treatment location. In some embodiments, the tapered portion 34 has a length, L4, from about 5 cm to about 30 cm, including lengths from about 10 cm to about 20 cm and from about 12 cm to about 17 cm. Furthermore, in some embodiments the tapered portion 34 is tapered along its entire length or is cylindrical along a portion of its length and tapered along another portion of its length.

In some embodiments, the tracking dilator 30 is formed of a radiopaque material, for example an elastomeric material with tungsten particles deposited therein. Similarly, the entry dilator 10 of FIG. 1 is formed of a radiopaque material in some embodiments.

FIG. 3 is a transverse cross sectional view of the tracking dilator 30 of FIG. 2, taken through line 3-3. This view illustrates the sidewall of the tracking dilator 30 in the tapered portion 34. In some embodiments, the central lumen 32 is located substantially along the central axis of the tracking dilator 30. Similarly, in some embodiments, the central lumen 22 of the entry dilator 10 of FIG. 1 is located along the central axis of the entry dilator 10.

FIG. 4 is a transverse cross sectional view of the tracking dilator 30 of FIG. 2, taken through line 4-4. FIG. 4 illustrates the position of the slot 33 within the main body 31 of the tracking dilator 30. FIG. 4 also shows the axial positioning of the tracking dilator 30 within the carotid sheath 60. FIG. 4 illustrates how, in some embodiments, the slot 33 is eccentrically positioned within the main body 31 of the tracking dilator 30. As also shown in FIG. 2, the slot 33 of the illustrated embodiment is in communication with the central lumen 32. The relationship between the slot 33 and the central lumen 32 may be understood as the central lumen 32 extending the entire length of the tracking dilator 30, with the central lumen 32 radially centered near the distal tip of the tracking dilator 30 and eccentrically positioned such that the central lumen 32 crosses the sidewall to the outside surface of the dilator (forming the slot 33) along the remaining length of the tracking dilator 30. Thus, the portion of the central lumen 32 that forms the slot 33 is only a partial lumen, as it is an open, or slotted, portion. In other embodiments the central lumen 32 is radially centered along the length of the tracking dilator 30, with the slot 33 extending from the central lumen 32 through the sidewall of the tracking dilator 30. The slot 23 of the entry dilator 10 of FIG. 1 may be similarly positioned as described in each embodiment described in connection with the slot 33 and the tracking dilator 30 of FIG. 2.

An exemplary procedure utilizing the entry and tracking dilators 10, 30 described in connection with FIGS. 1-4 begins by a physician first gaining access to the vascular system through the femoral artery at the groin. In some instances, a needle and a thin guidewire are used to initially pierce the wall of the artery. In this example, the thin guidewire is then used to advance a diagnostic catheter and/or a stiff guidewire to the treatment site. The physician then advances the entry dilator 10 along the stiff guidewire, the entry dilator 10 configured to push through calcified tissue at the entry site. In some instances the stiff guidewire extends all the way to, or beyond, a treatment site; for example, it may be anchored in the internal or external carotid arteries. Further, in some instances, the thin guidewire is initially advanced to, or beyond, the treatment site, and obviates the need for a stiff guidewire.

In this example, the guidewire and/or the entry dilator 10 is then used to advance the carotid sheath 40 such that it provides access to the treatment site. In some embodiments the distal end of the carotid sheath 40 will be positioned just proximal to the treatment site. In some instances, the carotid sheath 40 is relatively stiff, such that advancing the carotid sheath 40 along the guidewire poses a significant risk the guidewire will become displaced or dislodged, including instances where the distal end of the guidewire is moved from its anchor location. Thus, in some embodiments, the entry dilator 10 is used to advance the carotid sheath 40 to the treatment site and to mitigate the risk of dislodging the guidewire. In procedures where the path to the treatment site is relatively non-tortuous, an entry dilator 10 (with sufficient length to guide the carotid sheath 40 all the way to the treatment site) can be used to fully advance the carotid sheath 40.

In some instances, the tortuous path between the entry site and the treatment site renders the entry dilator 10 too stiff to facilitate advancement of the carotid sheath 40. Thus, in some embodiments, a practitioner exchanges the entry dilator 10 for a tracking dilator 30, then advances the carotid sheath 40 along the tracking dilator 30. (Note: in this example, the tracking dilator 30 of FIG. 2 may be used in connection with the same carotid sheath 40 as the entry dilator 10 of FIG. 1. Carotid sheath 40 can thus be used in place of carotid sheath 60 in connection with the tracking dilator 30.) This is done by advancing the tracking dilator 30 and the carotid sheath 40 along the guidewire, with the tracking dilator 30 protruding from the distal end of the carotid sheath 40. In some embodiments the tracking dilator 30 is softer than the carotid sheath 40 and is configured to facilitate advancement of the carotid sheath 40 along tortuous paths, such as from the aortic arch to either common carotid artery or beyond. Once the carotid sheath 40 is positioned, the practitioner then performs the remaining steps of the therapy, for example placing a stent.

In some embodiments where the entry dilator 10 is used prior to the tracking dilator 30, the slots 23, 33 are configured to allow rapid exchange of one dilator 10, 30 for the other. In some embodiments, the slots 23, 33 allow a practitioner to remove or insert a dilator 10, 30 while still grasping the guidewire relatively close to the entry site. As described above, if no slot 23, 33 were present, the length of the guidewire that extends proximally from the entry site would need to be longer than the total length of the dilator 10, 30 in order to allow a practitioner to directly grasp (or otherwise secure) the guidewire while removing the dilator 10, 30. In some embodiments, the slots 23, 33 are configured to allow the practitioner to decouple the dilator 10, 30 from the guidewire as the dilator 10, 30 is removed from the patient's body, without the need to feed the entire dilator 10, 30 over the proximal end of the guidewire. Thus, in some instances, the "rapid exchange" nature of these dilators 10, 30 reduces the risk that exchanging dilators 10, 30 will dislodge or displace the guidewire, as the practitioner is more able to maintain the stability and position of the guidewire due to the practitioner's ability to secure the guidewire near the entry point.

Furthermore, in some embodiments the distal end of the carotid sheath 40, 60 includes a hydrophilic coating. The outer surface of the entry and/or tracking dilator 10, 30 also includes a hydrophilic coating in some embodiments. This coating reduces friction, facilitating exchange of dilators 10, 30 and advancement of the carotid sheath 40, 60 along the dilators 10, 30.

FIG. 5 is a longitudinal cross section of a dilator 50 disposed within a carotid sheath 70. The carotid sheath 70 includes a radiopaque marker band 72. Similar to FIGS. 1 and 2, FIG. 5 illustrates the distal portions of the dilator 50 and the carotid sheath 70; the proximal ends are not shown. Any dilator 10, 30, 50 disclosed herein may be used in connection with any carotid sheath 40, 60, 70.

The illustrated dilator 50 is configured with a central lumen 52 positioned at a radially centered position in both the distal portion of the dilator 50 and a main body 51 of the dilator 50, unlike the lumens (22, 32) of the entry and tracking dilators 10, 30 that are eccentrically placed (and form slots 23, 33) along a portion of the dilators 10, 30.

In some embodiments, the dilator 50 is configured with a cylindrical portion 55 adjacent the distal end of the dilator 50. This cylindrical portion 55 defines a length, L5'. L5' is from about 3 cm to about 15 cm in some embodiments, including embodiments from about 5 cm to about 12 cm and embodiments from about 7 cm to about 11 cm. Furthermore, in some embodiments, the cylindrical portion 55 is formed in a relatively thin walled design, the wall of the dilator 50 being less than 0.025 inches in some instances, including wall thicknesses of less than 0.020 inches, less than 0.015 inches, and less than 0.010 inches.

Further, in the illustrated embodiment, the dilator 50 includes a tapered portion 54. The tapered portion 54 defines a length, L4', from about 5 cm to about 30 cm, including lengths from about 10 cm to about 20 cm and from about 12 cm to about 17 cm in some embodiments. Furthermore, like the tapered portion 34 of FIG. 2, in some embodiments the tapered portion 54 is tapered along its entire length or is cylindrical along a portion of its length and tapered along another portion of its length.

FIGS. 6 and 7 are transverse cross sectional views of portions of the dilator 50 of FIG. 5. FIG. 6 illustrates how the central lumen 52 may be axially centered within the tapered portion 54, while FIG. 7 illustrates how the central lumen 52, dilator body 51, and carotid sheath 70 may be concentrically positioned.

In some procedures, the dilator 50 is configured for use in place of both the entry dilator 10 and tracking dilator 30. For instance, if a patient does not have significant scar tissue or calcification at the entry site (for example, patients who have not had prior vascular surgery), a relatively stiff entry dilator may not be necessary. In such instances the dilator 50 of FIG. 5 is sufficiently stiff to allow for initial entry and subsequent guiding of the carotid sheath 70. Additionally, the dilator 50 is sufficiently pliable, particularly as related to the thin walled, cylindrical portion 55, to facilitate advancement of the dilator 50 along a difficult path for certain procedures. This design thus obviates the need for multiple dilators and the exchange of dilators in some instances. The dilator 50 herein described may be used in place of the entry dilator 10, the tracking dilator 30, or both in any of the exemplary procedures described above.

Any of the dilators 10, 30, 50 described herein may be composed of any elastomer or other material, including radiopaque materials such as plastics containing tungsten particles. Further, in some embodiments the dilator 10, 30, 50 is configured with a radiopaque marker band positioned at some point along the dilator 10, 30, 50, for example near the distal end. In some embodiments the radiopaque marker band is formed of a platinum alloy.

Moreover, in some embodiments any of the dilators 10, 30, 50 herein described may be configured with a coating to provide lubrication between the dilator 10, 30, 50 and the carotid sheath 40, 60, 70 thus aiding in the advancement of the carotid sheath 40, 60, 70 along the dilator 10, 30, 50.

The examples and embodiments disclosed herein are to be construed as merely illustrative and exemplary, and not as a limitation of the scope of the present disclosure in any way. It will be apparent to those having skill in the art with the aid of the present disclosure that changes may be made to the details of the above-described embodiments without departing from the underlying principles of the disclosure herein.

The invention claimed is:

1. A dilator for use in connection with a sheath, the dilator including:
   an elongate main body defining a distal end and a proximal end with distal and proximal portions extending therebetween;
   a lumen positioned within the elongate main body, and extending an entire length thereof, the distal portion defining a distal opening at the distal end of the elongate main body, wherein the lumen in the distal portion is radially centered; and
   a slot extending from the lumen through a sidewall of the elongate main body in the proximal portion, the slot extending longitudinally from the proximal end of the elongate main body, wherein the elongate main body and the slot define an eccentrically positioned portion of the lumen within the proximal portion;
   wherein the distal portion is disposed distal to the slot, the distal portion comprising a continuous circumference and wherein the slot extends along the remaining length of the elongate main body from the distal portion to the proximal end of the elongate main body.

2. The dilator of claim 1, wherein the slot extends along the majority of a length of the elongate main body, the length of the elongate main body extending from the proximal end of the elongate main body to the distal end of the elongate main body.

3. The dilator of claim 1, wherein the dilator is formed of a material having a durometer hardness of greater than 50 on the Shore D scale.

4. The dilator claim 1, wherein the dilator is configured to extend at least 10 cm beyond a distal end of the sheath.

5. The dilator of claim 4, wherein the dilator is formed of a material having a durometer hardness of less than or equal to 45 on the Shore D scale.

6. The dilator of claim 4, wherein the dilator includes a non-tapering cylindrical portion adjacent the distal end of the dilator.

7. The dilator of claim 6, wherein the non-tapering cylindrical portion is at least 3 cm in length.

8. The dilator of claim 6, wherein the non-tapering cylindrical portion has a sidewall thickness of less than 0.010 inches.

9. The dilator of claim 6, wherein the dilator forms a tapered portion adjacent the non-tapering cylindrical portion.

10. The dilator of claim 9, wherein the tapered portion is at least 10 cm in length.

11. The dilator of claim 1, wherein the dilator is formed of a radiopaque material.

12. The dilator of claim 1, wherein the dilator includes a radiopaque marker band adjacent the distal end of the dilator.

13. The dilator of claim 1, further including a lubricity coating.

14. A sheath assembly including:
   an elongate sheath;
   an entry dilator including:
   an elongate main body defining a distal end and a proximal end with distal and proximal portions extending therebetween;
   a lumen positioned within the main body, and extending an entire length thereof, the distal portion defining a distal opening at the distal end of the elongate main body, wherein the lumen in the distal portion is radially centered; and
   a slot extending from the lumen through a sidewall of the entry dilator in the proximal portion, the slot extending longitudinally from the proximal end of the elongate main body, wherein the elongate main body and the slot define an eccentrically positioned portion of the lumen within the proximal portion;
   wherein the distal portion is disposed distal to the slot, the distal portion comprising a continuous circumference and wherein the slot extends along the remaining length of the elongate main body from the distal portion to the proximal end of the elongate main body; and
   a tracking dilator including:
   an elongate main body defining a distal end and a proximal end with distal and proximal portions extending therebetween;
   a lumen positioned within the elongate main body, and extending an entire length thereof, the distal portion defining a distal opening at the distal end of the elongate main body, wherein the lumen in the distal portion is radially centered;
   a non-tapering cylindrical portion adjacent the distal end of the elongate main body; and
   a slot extending from the lumen through a sidewall of the tracking dilator in the proximal portion, the slot extending longitudinally from the proximal end of the elongate main body, wherein the elongate main body and the slot define an eccentrically positioned portion of the lumen within the proximal portion;
   wherein the distal portion is disposed distal to the slot, the distal portion comprising a continuous circumference and wherein the slot extends along the remaining length of the elongate main body from the distal portion to the proximal end of the elongate main body.

15. The sheath assembly of claim 14, further including:
   a third dilator including:

an elongate main body defining a distal end and a proximal end; and a lumen positioned within the elongate main body, defining a distal opening at the distal end of the elongate main body;

a non-tapering cylindrical portion adjacent the distal end of the elongate main body; and a tapered portion proximal of and adjacent to the non-tapering cylindrical portion;

wherein the third dilator is formed of a material having a durometer hardness of less than or equal to 45 on the Shore D scale.

16. A rapid exchange dilator designed for placement of a carotid sheath into a patient's carotid artery, the dilator having an elongate main body and a lumen extending an entire length of the elongate main body, the lumen comprising a centrally located circular portion at a distal end defining a distal opening and having a slot at a proximal portion, the slot extending from the lumen through an outer wall of the dilator and extending longitudinally from a proximal end of the dilator to a distal portion, the distal portion comprising a continuous circumference from the distal end to the proximal portion, and wherein the slot extends along the remaining length of the elongate main body from the distal portion to the proximal end of the elongate main body, the slot disposed along most of the length of the dilator, wherein the elongate main body and slot define an eccentrically positioned section of the lumen.

17. The rapid exchange dilator of claim 16 where the dilator is an entry dilator explicitly designed for entry through the patient's skin and into the patient's femoral artery at the groin, the dilator being formed from a plastic material that is comparatively hard with a Shore D durometer that is greater than 50.

18. The rapid exchange dilator of claim 16 where the dilator is a tracking dilator explicitly designed to be easily advanced over a guidewire that has been placed through a carotid stenosis without pulling that guidewire out of the stenosis, the dilator configured to extend beyond the end of the carotid sheath at least 10 cm and the dilator being formed from a plastic material that is comparatively soft with a Shore D durometer that is equal to or less than 45.

19. The rapid exchange tracking dilator of claim 18 where a distal portion of the dilator is a thin-walled cylindrical tube having a length of at least 3 cm and a remaining portion of the dilator that is configured to lie distal to the distal end of the carotid sheath is a generally tapered section with its largest diameter configured to be situated at the distal end of the carotid sheath and the distal end of the remaining portion having the same diameter as the thin-walled cylindrical tube, the length of the tapered section of the dilator being at least 10 cm.

20. The rapid exchange dilator of claim 16 where the dilator is formed from a plastic that is filled with metallic particles so as to make the dilator radiopaque.

21. The rapid exchange dilator of claim 16 where the dilator has a radiopaque marker band located at or near the distal end of the dilator.

22. A tracking dilator designed to be advanced over a guidewire that has been placed through a stenosis in a carotid artery, the tracking dilator also being designed to advance a carotid sheath into a carotid artery of a human patient, the tracking dilator comprising: an elongate main body having distal and proximal portions defining distal and proximal ends; the distal portion of the dilator being a thin-walled cylindrical tube having a length of at least 3 cm and a remaining portion of the dilator that is configured to lie distal to the distal end of the carotid sheath having a generally tapered section with its largest diameter configured to be situated at the distal end of the carotid sheath and the distal end of the remaining portion having the same outer diameter as the thin-walled cylindrical tube, the length of the tapered section of the dilator being at least 5 cm, the tracking dilator having a lumen extending for an entire length of the dilator thereby making the dilator an over-the-wire dilator, the tracking dilator comprising a slot along a proximal portion of the elongate main body extending from the lumen through a sidewall of the dilator, the slot extending longitudinally from the proximal end of the dilator to a point proximal of the thin-walled cylindrical tube, and wherein the slot extends along the remaining length of the elongate main body, from the thin-walled cylindrical tube to the proximal end of the elongate main body, the elongate main body and the slot define an eccentrically positioned section of the lumen, the dilator also being formed from a comparatively soft plastic material that has a Shore D durometer that is equal to or less than 45.

23. The tracking dilator of claim 22 where the dilator is formed from a plastic that is filled with metallic particles so as to make the dilator radiopaque.

24. The tracking dilator of claim 22 where the dilator has a radiopaque marker band located at or near the distal end of the dilator.

25. The tracking dilator of claim 22 where the dilator has a lubricity coating so as to enhance its ability to pass through tortuous arteries.

* * * * *